(12) United States Patent
Wanke et al.

(10) Patent No.: US 8,482,739 B1
(45) Date of Patent: Jul. 9, 2013

(54) HETERODYNE PHOTOMIXER SPECTROMETER WITH RECEIVER PHOTOMIXER DRIVEN AT DIFFERENT FREQUENCY THAN SOURCE PHOTOMIXER

(75) Inventors: Michael C. Wanke, Albuquerque, NM (US); Kevin Fortier, Albuquerque, NM (US); Eric A. Shaner, Rio Rancho, NM (US); Todd A. Barrick, Albuquerque, NM (US)

(73) Assignee: Sandia Corporation, Albuquerque, NM (US)

( * ) Notice: Subject to any disclaimer, the term of this patent is extended or adjusted under 35 U.S.C. 154(b) by 532 days.

(21) Appl. No.: 12/892,625

(22) Filed: Sep. 28, 2010

Related U.S. Application Data

(60) Provisional application No. 61/257,486, filed on Nov. 3, 2009.

(51) Int. Cl.
*G01B 9/02* (2006.01)
*G01J 5/02* (2006.01)

(52) U.S. Cl.
USPC .................... 356/484; 356/451; 250/341.1

(58) Field of Classification Search
USPC ............ 356/451, 484; 250/350, 351, 339.01, 250/339.05–339.07, 339.11–339.13
See application file for complete search history.

(56) References Cited

U.S. PATENT DOCUMENTS

| | | | |
|---|---|---|---|
| 7,936,453 B2 * | 5/2011 | Logan et al. | 356/300 |
| 2004/0065832 A1 * | 4/2004 | Cluff et al. | 250/341.1 |

OTHER PUBLICATIONS

Deninger, Preciesely tunable continuous-wave terahertz source with interferometric frequency control, Review of Scientific Instruments, 79, 044702-1 thru 044702-6 (2008).
Matsuura, A Tunable Cavity-Locked Diode Laser Source for Terahertz Photomixing, IEEE Transactions on Microwave Theory and Techniques, vol. 48, No. 3, Mar. 2000, 380-387.
Oh, High-sweeping-speed optically synchronized dual-channel terahertz-signal generator for driving a superconducting tunneling mixer and its application to active gas sensing, Optics Express, vol. 17, No. 21, Oct. 12, 2009, 18455-18461.
Shaner, Time-resolved impulse response of the magnetoplasmon resonance in a two-dimensional electron gas, Physical Review B 66, 041402(R) (2002).
Shaner, Picosecond electrical excitation of a two-dimensional electron gas, Proc. of SPIE, vol. 5352, 2004, 364-371.
Verghese, Generation and detection of coherent terahertz waves using two photomixers, Applied Physics Letters, vol. 73, No. 26, Dec. 29, 1998, 3824-3826.
Verghese, Highly Tunable Fiber-Coupled Photomixers with Coherent Terahertz Output Power, IEEE Transactions on Microwave Theory and Techniques, vol. 45, No. 8, Aug. 1997, 1301-1309.
Zamdmer, On-chip frequency-domain submillimeter-wave transceiver, Applied Physics Letters, vol. 75, No. 24, Dec. 13, 1999, 3877-3879.

* cited by examiner

*Primary Examiner* — Hwa Lee
(74) *Attorney, Agent, or Firm* — Kevin W. Bieg

(57) ABSTRACT

A heterodyne photomixer spectrometer comprises a receiver photomixer that is driven at a different frequency than the source photomixer, thereby maintaining the coherent nature of the detection, eliminating etalon effects, and providing not only the amplitude but also the phase of the received signal. The heterodyne technique can be applied where the source and receiver elements are components of a waveguide thereby forming an on-chip heterodyne spectrometer.

17 Claims, 3 Drawing Sheets

HETERODYNE PHOTOMIXER SPECTROMETER WITH RECEIVER PHOTOMIXER DRIVEN AT DIFFERENT FREQUENCY THAN SOURCE PHOTOMIXER

CROSS-REFERENCE TO RELATED APPLICATION

This application claims the benefit of U.S. Provisional Application No. 61/257,486, filed Nov. 3, 2009, which is incorporated herein by reference.

STATEMENT OF GOVERNMENT INTEREST

This invention was made with Government support under contract no. DE-AC04-94AL85000 awarded by the U.S. Department of Energy to Sandia Corporation. The Government has certain rights in the invention.

FIELD OF THE INVENTION

The present invention relates to spectroscopy and, in particular, to a heterodyne photomixer spectrometer that can be used for terahertz spectroscopy.

BACKGROUND OF THE INVENTION

Spectroscopy in the terahertz (THz) frequency range has the potential to provide highly specific identification of molecular species in gas sensing applications. To take full advantage of what THz spectroscopy can offer, resolution on the order of megahertz (MHz) combined with the ability to tune by at least 1 THz is needed. One of the best ways currently to generate widely tunable THz radiation with the requisite resolution is to illuminate an electrically biased photomixer with two visible or near-IR lasers that operate at slightly different and tunable frequencies and generate a THz signal at the difference frequency. This has the advantage of using commercially available laser systems and operates at room temperature. Unfortunately, existing photomixers generate relatively small amounts of power (typically less than 1 microwatt).

The simplest way to detect a swept frequency source is to use a broadband direct detector that is sensitive only to the power incident on it. Unfortunately, in the THz frequency range direct detectors operating at room temperature are not very sensitive. Cryogenic cooling can increase the sensitivity, but limit the usefulness. Even with higher sensitivity, direct detection is still a problem with a broadband detector, since the power of the background radiation of objects at room temperature integrated over the frequency bandwidth of the detector can easily exceed the low power from the sources. Using an optical filter to limit the bandwidth is not beneficial unless the filter transmission is incredibly narrow and can be tuned to always peak at the THz frequency. At the moment such a filter does not exist.

One technique that has been used to increase the signal-to-noise employed (and is used in existing commercial systems) is to employ coherent homodyne detection. In this case, a second unbiased photomixer illuminated by the same two lasers will produce a finite DC current when also illuminated by the THz beam generated by the other photomixer. The direct current generated by other frequencies averages to zero (at least for frequencies that are further away from the desired frequency by more than the inverse of the measurement time). Since both detectors are illuminated by the same two laser sources, the detector spectral response is always centered on the source frequency. In this way, detection of the background radiation at other frequencies is significantly reduced, while sensitivity and speed are enhanced.

However, homodyne detection has a different problem. The detecting element does not respond to the intensity of the emitted beam, but the electric field instead. Because of this, the magnitude of the current depends on the relative phase of the THz signal reaching the detector and the phase of the beat frequency of the two visible lasers incident on the detector. This phase depends on the distance (measured in wavelengths) separating the source and detector. Therefore as the frequency is tuned the detector signal will vary even if the output power, the physical separation between the source and detector, and the transmission through the intervening media are constant. While this can of course be calibrated out, the signal-to-noise will vary with frequency, and at certain frequencies spectra will not be obtained. To compensate for this, data from multiple scans can be collected where each scan uses a different source/detector separation. However, this increases the measurement time and requires stable targets. In addition, by detecting a response at DC frequencies, 1/f type flicker noise adds significant noise.

Therefore, a need remains for a heterodyne photomixer spectrometer that enables room temperature, high resolution, and high speed detection of both amplitude and phase in a small package.

SUMMARY OF THE INVENTION

The present invention is directed to a heterodyne photomixer spectrometer, comprising a first laser beam that is focused onto a source photomixer, a second laser beam that is focused onto a receiver photomixer and that is at a stable difference frequency ($\delta$), from the first laser beam, and a third laser beam that is focused on both the source and the receiver photomixers and is swept in frequency, wherein the light output from the source photomixer is directed onto a sample and the light transmitted through the sample is detected by the receiver photomixer. The frequency different between the two photomixers, $\delta$, is chosen so that standard electronics can pull out the amplitude. While a spectrum analyzer can be used to measure the amplitude and phase, since $\delta$, always remains fixed, a simple electronic filter with a peak transmission centered at $\delta$ can also be used to measure the amplitude, simplifying the electronics required. Because the receiver photomixer is driven at a different frequency than the source photomixer, the coherent nature of the detection is maintained and both the amplitude and the phase of the received signal can be detected without having to change the path length and take multiple scans. The heterodyne technique can be applied where the source and receiver elements are components of a waveguide thereby forming an on-chip heterodyne spectrometer.

BRIEF DESCRIPTION OF THE DRAWINGS

The accompanying drawings, which are incorporated in and form part of the specification, illustrate the present invention and, together with the description, describe the invention. In the drawings, like elements are referred to by like numbers.

DETAILED DESCRIPTION OF THE INVENTION

Figure 1:
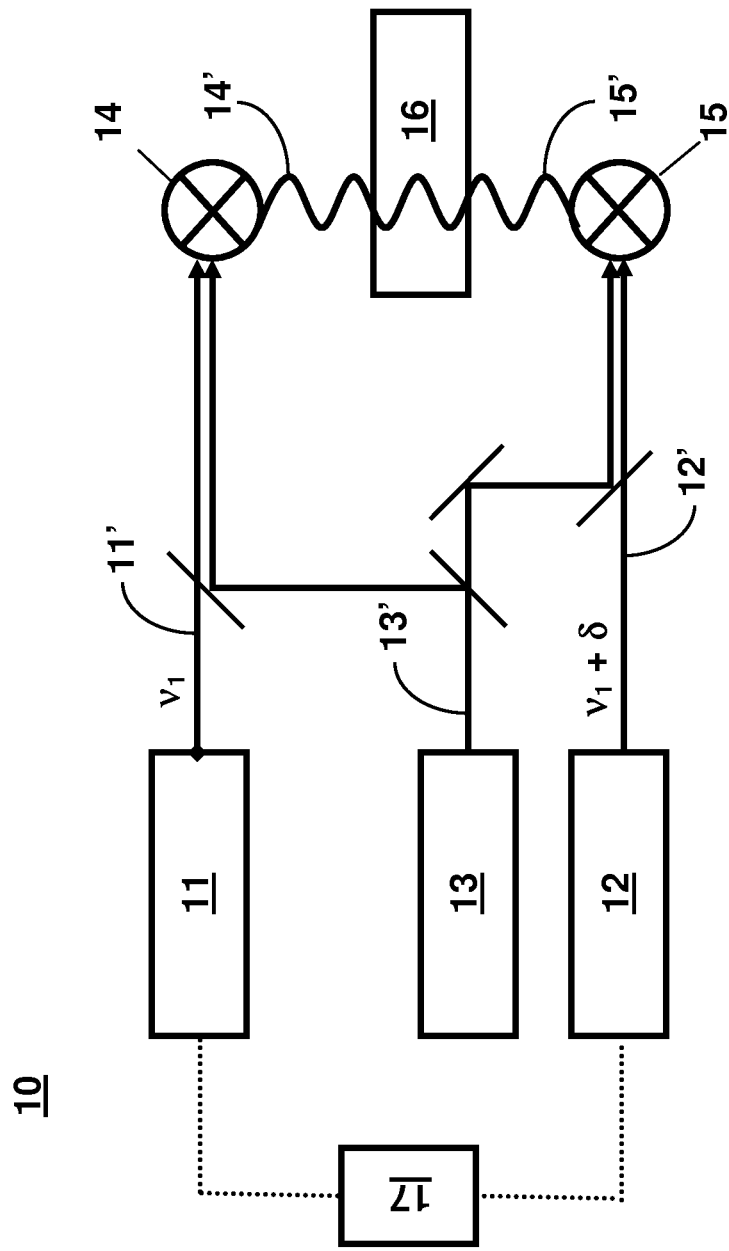
FIG. 1 is a schematic illustration of heterodyne photomixer spectrometer that uses three lasers for coherent detection without suffering from path length versus sweep frequency etalon effects.

FIG. 1 is a schematic illustration of a heterodyne photomixer spectrometer 10 that can be used for terahertz spectroscopy of a sample 16 (for example, a gas sample). The spectrometer 10 comprises an emitter source 14 and receiver 15. Preferably, the frequency difference and phase between the source 14 and receiver 15 is very stable. Thus, the frequencies of two visible or near-IR lasers 11 and 12 can be locked 17 such that they are different by a stable frequency difference $\delta$. For example, in one possible implementation of frequency locking, the second laser beam 12' can be generated by passing a portion of the first laser beam 11' through an acousto-optic modulator (AOM) or electro-optic modulator (EOM) driven at the desired difference frequency, $\delta$, to generate a weaker laser beam at $v_1+\delta$, and then amplifying the weaker laser beam to generate the second laser beam 12' at $v_1+\delta$. For example, the frequency difference can be between approximately 1 MHz for an AOM an approximately 1 GHz for an EOM. The amplifier can be a Master-Oscillator-Power-Amplifier (MOPA), although an amplifier may not be required for some applications (particularly when using an EOM). Each laser beam 11' or 12' is focused onto only one of the photomixers 14 or 15. A third laser beam 13' from a tunable laser 13 can be focused onto both photomixers 14 and 15 using beam splitters and its frequency can be swept. The source photomixer 14 will generate radiation 14' at the difference frequency between lasers 11 and 13. The difference frequency can be tuned by changing the frequency of either laser 11 or 13. The light output 14' from the source photomixer 14 is directed onto the sample 16 and the light 15' transmitted, reflected, or guided through the sample is detected by the receiver photomixer 15. The instantaneous response of the detector depends on the electric field incident from the beam 15' emitted by the source photomixer and the phase of the beat frequency between laser beams 12' and 13' which are also incident on the mixer detector 15. Since the frequency generated by the source mixer is different by $\delta$ than the beat frequency on the mixer detector, the response of the detector 15 will oscillate at $\delta$. The detector 15 can be connected to a spectrum analyzer to measure the amplitude of the frequency response at the difference frequency $\delta$. Alternatively, since $\delta$ is fixed an electronic filter can be centered on the response of the receiver photomixer at the difference frequency and a power meter can be used to measure the amplitude of the passed response. For example, setting the frequency offset to 1 MHz removes the response from being a DC response, where significant 1/f noise is present, and also allows the use of low-noise amplifiers that are common around 1 MHz. Because the measurement is a heterodyne measurement, the coherent instrumental etalon effects are removed. Heterodyne (instead of homodyne) means that the amplitude and phase are decoupled and separately measurable. For sweeping the frequency of the beam interacting with the sample, the frequency of laser 11 or laser 13 can be swept as long as the frequency difference between lasers 11 and 12 can be maintained. With an AOM or EOM used to determine the frequency of laser 12, this difference frequency is certain. For the largest tuning range, lasers 11 and 13 can both be varied.

The heterodyne technique can be applied where the source and receiver elements are components of a waveguide thereby forming an on-chip heterodyne spectrometer. The on-chip heterodyne spectrometer is directly analogous to the free-space heterodyne photomixer spectrometer described above in terms of signal generation and detection. However, the propagating waves in the on-chip spectrometer are confined to a waveguiding structure (such as a coplanar waveguide, coplanar transmission line, or microstrip) rather than propagating in free space.

Figure 2:
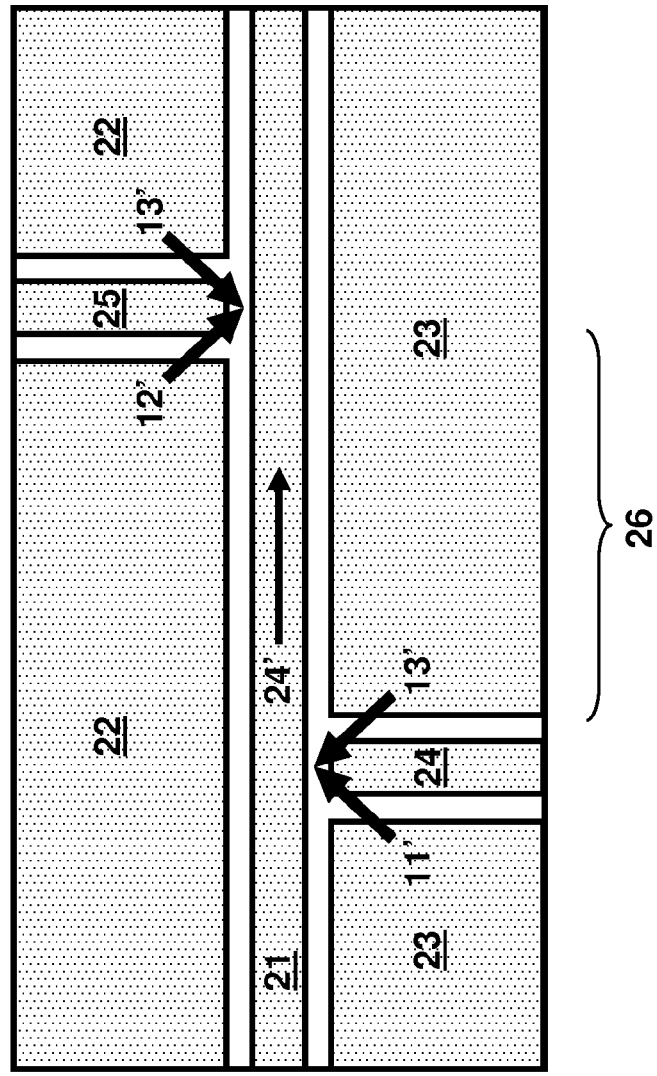
FIG. 2 shows a top-view schematic illustration of an on-chip heterodyne spectrometer that uses a coplanar waveguide to confine the propagating electromagnetic waves.

FIG. 2 shows a top-view schematic illustration of exemplary an on-chip heterodyne spectrometer 20 that uses a coplanar waveguide (CPW) to confine the propagating electromagnetic waves. The CPW comprises a signal conductor 21 that is separated from a pair of coplanar ground conductors 22 and 23. Optoelectronic switches are provided by the gaps between metal bias lines 24 and 25 and the signal conductor line 21. These optoelectronic switches can be used as the emitter source and receiver, respectively. Therefore, the first laser beam 11' and third laser beam 13' of the heterodyne spectrometer configuration described previously illuminate the emitter source gap between metal bias line 24 and signal conductor 21 thereby generating an electromagnetic wave 24' that propagates on the signal conductor 21 of the CPW. The signal wave can be detected at the receiver gap between metal bias line 25 and signal conductor 21 that is illuminated by the second laser beam 12' and the third laser beam 13'. The detected signal can be processed in the same way as the receiver photomixer previously described.

Figure 3:
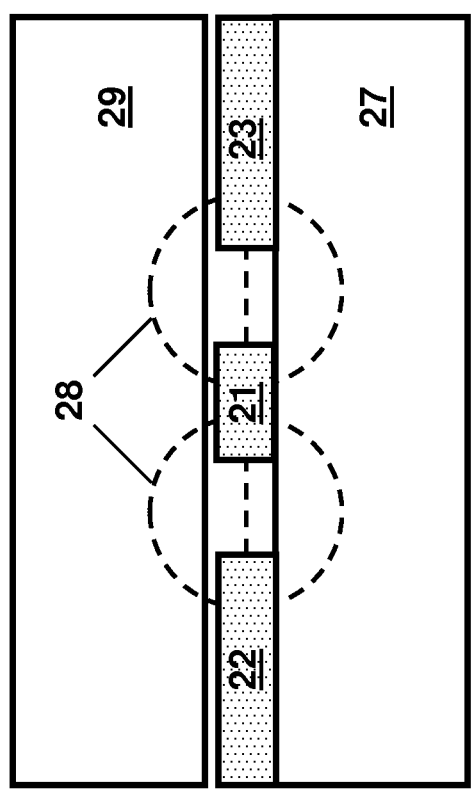
FIG. 3 shows a cross-sectional end view illustration of an on-chip heterodyne spectrometer that can be used to characterize a material under test in a sample portion of the coplanar waveguide.

FIG. 3 shows a cross-sectional end view illustration of an on-chip heterodyne spectrometer that can be used to characterize a material under test (MUT) in a sample portion 26 of the CPW between the emitter optoelectronic switch and the receiver optoelectronic switch. The CPW comprises a signal conductor 21 that is separated from a pair of coplanar ground conductors 22 and 23 on a dielectric substrate 27. Although the electric and magnetic fields are guided by the waveguide conductors 21, 22, and 23, the electromagnetic field extends or 'fringes' beyond the waveguide surface. Therefore, fringing fields 28 exist above and below the metallic conductors, particularly when using thin conductors or large gaps separating the conductors. In this example, the MUT 29 is placed on the top of the CPW for material measurement. The fringing fields 28 interact with the MUT 29 allowing spectroscopic information to be obtained from the electromagnetic wave that is transmitted through the sample portion 26 of the CPW and detected by the receiver, as described above.

The present invention has been described as a heterodyne photomixer spectrometer. It will be understood that the above description is merely illustrative of the applications of the principles of the present invention, the scope of which is to be determined by the claims viewed in light of the specification. Other variants and modifications of the invention will be apparent to those of skill in the art.

We claim:

1. A heterodyne photomixer spectrometer, comprising:
  a first laser generating a first laser beam,
  a second laser generating a second laser beam at a frequency having a stable difference, $\delta$, from the frequency of the first laser beam,
  a third laser generating a third laser beam swept in frequency,
  a source photomixer receiving the first laser beam and third laser beam and outputting light onto a sample, and
  a receiver photomixer receiving the second laser beam and third laser beam and detecting the light transmitted reflected, or guided through the sample.

2. The heterodyne photomixer spectrometer of claim 1, further comprising a spectrum analyzer connected to the receiver photomixer to measure the amplitude of the frequency response at the difference frequency.

3. The heterodyne photomixer spectrometer of claim 1, further comprising an electronic filter centered on the response of the receiver photomixer at the difference frequency to pass only the difference frequency.

4. The heterodyne photomixer spectrometer of claim 3, further comprising a power meter to measure the amplitude of the passed response of the electronic filter.

5. The heterodyne photomixer spectrometer of claim 1, wherein the stable frequency difference is between approximately 1 MHz and 1 GHz.

6. The heterodyne photomixer spectrometer of claim 1, wherein the first and second lasers are visible lasers.

7. The heterodyne photomixer spectrometer of claim 1, wherein the first and second lasers are near-infrared lasers.

8. The heterodyne photomixer spectrometer of claim 1, wherein the second laser beam is generated by passing a portion of the first laser beam through an acousto-optic modulator (AOM) driven at the desired difference frequency, $\delta$, to generate a weaker laser beam at $v_1+\delta$ and wherein this weaker laser beam is amplified to generate the second laser beam at $v_1+\delta$.

9. The heterodyne photomixer spectrometer of claim 8, wherein the amplifier used to generate the second laser beam is a Master-Oscillator-Power-Amplifier (MOPA).

10. The heterodyne photomixer spectrometer of claim 1, wherein the second laser beam is generated by passing a portion of the first laser beam through an electro-optic modulator (EOM) driven at the desired difference frequency, $\delta$, to generate the second laser beam at $v_1+\delta$.

11. The heterodyne photomixer spectrometer of claim 10, wherein a Master-Oscillator-Power-Amplifier (MOPA) boosts the power of the second laser beam.

12. The heterodyne photomixer spectrometer of claim 1, wherein the sample comprises a gas.

13. The heterodyne photomixer spectrometer of claim 12, wherein the gas is contained in a gas cell.

14. The heterodyne photomixer spectrometer of claim 1, wherein the source and receiver photomixers are both on the same chip and connected via an on chip waveguide.

15. The heterodyne photomixer spectrometer of claim 14, wherein the source or receiver photomixer comprises an optoelectronic switch.

16. The heterodyne photomixer spectrometer of claim 14, wherein the waveguide comprises a coplanar waveguide, coplanar transmission line, or microstrip.

17. The heterodyne photomixer spectrometer of claim 14, wherein the sample is placed close to or on the waveguide so that the fringing fields of the electromagnetic wave propagating between the source and receiver photomixers interact with the sample.

* * * * *